(12) United States Patent
Pitha

(10) Patent No.: US 6,884,790 B2
(45) Date of Patent: Apr. 26, 2005

(54) VERIFIABLE ABSORPTION DRUG DELIVERY FORM BASED ON CYCLODEXTRINS

(76) Inventor: Josef Pitha, 5809 Nicholson La., Unit 1405, Rockville, MD (US) 20852

( * ) Notice: Subject to any disclaimer, the term of this patent is extended or adjusted under 35 U.S.C. 154(b) by 0 days.

(21) Appl. No.: 10/653,111

(22) Filed: Sep. 3, 2003

(65) Prior Publication Data

US 2004/0048831 A1 Mar. 11, 2004

Related U.S. Application Data

(60) Provisional application No. 60/408,896, filed on Sep. 9, 2002.

(51) Int. Cl.[7] .......................... C08B 37/16; C07H 1/00; A61K 31/724
(52) U.S. Cl. ........................ 514/58; 536/103; 536/124
(58) Field of Search ............................ 536/103, 124; 514/58

(56) References Cited

U.S. PATENT DOCUMENTS 5,134,127 A  *  7/1992  Stella et al. .................. 514/58

FOREIGN PATENT DOCUMENTS

HU              54506      *    3/1991

* cited by examiner

Primary Examiner—James O. Wilson
Assistant Examiner—Everett White
(74) Attorney, Agent, or Firm—Glenna Hendricks

(57) ABSTRACT

Solid dosage forms are produced by absorbing solutions of drug:cyclodextrin inclusion complexes on absorbing matrices and then drying. The matrices may, but need not, disintegrate in water. The resulting forms are suitable for oral or sublingual administration, and also can be used in topical administrations to mucosa covered tissues. They are particularly suitable for sublingual administration because the eluted, nondisintegrated matrix (e.g., absorbing paper) can be recovered and checked for completion of elution. This enables documentation that effective absorption occurred from the mouth cavity.

11 Claims, No Drawings

VERIFIABLE ABSORPTION DRUG DELIVERY FORM BASED ON CYCLODEXTRINS

This application takes priority from U.S. provisional application No. 60/408,896 filed Sep. 9, 2002.

FIELD OF INVENTION

The present invention relates to pharmaceutical preparations of solid dosage forms for drugs that form complexes with cyclodextrins.

BACKGROUND OF THE INVENTION

Starting materials for the production of solid dosage forms for drugs generally are in the form of powders. In the conventional processing mode, these powders are mixed thoroughly to achieve homogeneity and the resulting mixture is filled into capsules or compressed into tablets either directly or after granulation. Obtaining suitable product requires multiple auxiliary ingredients such as diluents, binders, lubricants, glidants, disintegrands, and stabilizers. Furthermore, auxiliary ingredients must be specifically formulated in correct proportions adapted to the particular drug and processing equipment. These prior art methods are well suited for batch production. However, continuous production methods present issues not addressed by methods used for batch production. Furthermore, batch production is slower, less economical and requires intermittent sampling to maintain quality control, since it is not possible to test every tablet for the correct amount of ingredients.

Conventional batch methods can be used for almost all drugs with satisfactory results. However, specific instances allow the use of more economical approaches. Using the methods of the instant invention, it is possible to administer many drugs in the form of water-soluble inclusion complexes and use a simpler, continuous production process.

Cyclodextrins are a group of compounds consisting of or derived from the three parent cyclodextrins: alpha- beta- and gamma-cyclodextrins. Parent cyclodextrins are often chemically derivatized to improve their properties. Examples of such derivatives include partial methyl, hydroxypropyl or sulfoalkyl ethers, or partial acetyl esters of parent cyclodextrins. Cyclodextrins have numerous uses based on their ability to solubilize chemicals through formation of complexes, which are of inclusion type and form spontaneously. Some cyclodextrins by themselves can form films, but are not gel forming agents.

Cyclodextrin complexes of drugs dissolve rapidly in water and, consequently, are especially well suited for administration of drugs that should be absorbed from the mouth cavity. Drugs absorbed from the mouth cavity directly enter blood circulation, whereas drugs absorbed from the rest of the gastrointestinal tract enter blood circulation only after passage through the liver, where many drugs are destroyed. This was exemplified by administration of cyclodextrin complexes of sex hormones in U.S. Pat. No. 4,596,795. Data in that patent showed that, when a hormone was absorbed from the mouth, it entered into blood circulation rapidly and efficiently, while when absorbed from the stomach, only a small amount slowly entered the blood stream. Drugs in appropriate carriers that are absorbed from the mouth have the potential to replace compositions for parenteral administration (i.e., injections) for use where rapid effects are required (e.g., migraine headaches). For desired absorption to occur effectively, it is critical that the cyclodextrin:drug inclusion complex be in direct contact with the oral mucosa; then, the drug (and not cyclodextrin) is absorbed. Furthermore, the drug is not swallowed and absorption occurs through the mucous membrane of mouth directly into the blood stream. For convenience, it is important that total time of administration is brief. In previous art (U.S. Pat. No. 4,596,795 and clinical studies based on this patent including C. A. Stuenkel et al., Journal of Clinical Endocrinology and Metabolism, 72, 1054–1059, 1991; E. Salehian et al., ibid, 80, 3567–3575, 1995; H. Fridriksdottir et al., Pharmazie, 51, 39–42, 1996) conventional tablets containing cyclodextrin complexes of sex hormones were used; that is, ingredients were in the form of powders.

Regarding prior art, the following publications direct to solid dosage forms different from conventional tablets. Historical formulations predating tablets include medicated papers. These were blotting papers soaked in solution of a medicinal (e.g., iodine), dried, and used by pressing directly against the skin or mucosal surface. Medicated papers were in universal use at the beginning of the twentieth century (D. Hunter: Papermaking, Dover Publishers, Inc., 1974). Presently, other forms have almost completely replaced them.

In U.S. Pat. No. 4,349,531, solid pharmaceutical forms on laminates of webs or on paper compositions are described. In these forms, the medication is deposited on surfaces of these webs in fine particulate form, that is, not dissolved. Similar webs are described in U.S. Pat. No. 4,180,558, improved by making them from carboxymethylcellulose paper. Use of that type of paper prevents layers from sticking together when the solid dosage must be made of stacks of paper to carry the amount of drug to be administered.

In U.S. Pat. No. 5,629,003, a dosage form containing an active ingredient, film-formers, gel-formers and fillers was extruded and dried either alone or spread onto nonabsorbing carrying paper from which it could be released. The dosage itself is specified to be rapidly disintegrating. Cyclodextrins in that patent are listed as fillers with emphasis that they are present in the product in substantially undissolved form (page 9) and not specified to form inclusion complexes. A gel-forming agent is declared necessary.

There is art teaching cyclodextrins are permanently bound to cellulose or cellulose based materials by chemical bonds. The medicinal is complexed to such immobilized cyclodextrins; for example, Hungarian Patent 54,506. Upon moistening such a composite, only the medicinal, and not the cyclodextrin, is released. Thus, there is no carrier that can carry the medicinal to its absorption site. Release of medicinal (and the following absorption into tissue) is consequently a slow process. In the case of the instant invention, the cyclodextrin is not permanently bound to the cellulosic material.

SUMMARY OF THE INVENTION

The instant invention uses drug:cyclodextrin inclusion complexes to optimize production and use of solid dosage forms. The instant invention uses solutions of drug:cyclodextrin inclusion complexes directly from their preparation, that is, without the evaporation step used previously. The solution is absorbed directly into a solid matrix which is then processed into the desired solid dosage form. As a consequence, the instant process provides improvement by (a) reducing the number of steps, (b) providing common processing procedures for various drugs with easy cleanup in between runs, (c) establishing easily effective continuous manufacturing processes, and (d) providing for continuous quality control. For drugs that must be absorbed from the mouth cavity, the invented dosage form has the added advantage of assuring correct administration.

DETAILED DESCRIPTION OF THE INVENTION

Drug:cyclodextrin inclusion complexes were made by dissolution of a cyclodextrin in water, which may optionally contain a co-solubilizer, then adding the drug to this solution and stirring until saturation has occurred. Thereafter, the solutions were clarified by filtration or centrifugation. It is a clear advantage to use a high concentration of cyclodextrin. In Example 1, concentrations up to 50% (w/w) cyclodextrin in water were used when dissolutions were performed at room temperature; at elevated temperatures, the concentration of cyclodextrin can be increased. The amount of drug dissolved through such complex formation can be up to one tenth of the amount of cyclodextrin used.

Such solutions were handled without difficulty. Their technically important properties are similar to those of sucrose of the same concentration. Solutions of various drugs complexed with cyclodextrins have similar technically important properties as liquids. Thus the same processing and instrumentation can be used for different drugs. The studies showed that the solutions of drug:cyclodextrin do not have to be dried to powders to be processed into solid dosage forms and can be used directly. The solutions were absorbed into absorbent matrices and then dried, leaving behind the drug and cyclodextrin distributed through the matrix of material. The term "absorbing or absorbent matrix" is used here to mean inert materials, which are wettable by water-containing solvents and will retain aqueous liquids. An example of an absorbing matrix that does not disintegrate in water is filtration or blotting paper. Examples of absorbing matrices that do disintegrate are cellulose powder, starch and lactose. Two forms of absorbent matrices were used in the examples; (1) sheets which were later stamped into disks and (2) powders that were formulated into a paste by cyclodextrin or drug:cyclodextrin solutions. After absorption of drug solutions into the matrices, these were dried. That such absorption and drying can lead to a useful product was demonstrated experimentally.

The absorbing matrix must be able to absorb enough of the solution of drug:cyclodextrin inclusion complex so that excessive amounts of material do not cause discomfort. Example 1 evaluates the carrying capacity of samples of filtration paper and polypropylene filtration cloth. Disks of filtration paper can be used to carry up to 5 mg of active drug, whereas polypropylene filtration cloth can be used to carry up to 20 mg of an active drug. These are useful amounts, especially when administered sublingually. Steroid hormones mentioned typically are administered in up to 10 mg doses; 20 mg doses are effective for use of their precursors (e.g., for androstenediol cmp. G. A. Brown et al., Journal of Applied Physiology, 92, 142–146, 2002). Choice of thicker sheets, or their modification can further increase the carrying capacity.

The properties of the carrier wetted with drug solution must be such that it can be handled without loss of the drug:cyclodextrin inclusion complex and must enable effective quantification of the amount of drug deposited. The combination of results in Examples 1 and 2 show that with the saturation of paper used there, all of the drug absorbed can be recovered. Obviously, mechanical properties of the wetted matrix are good enough to enable handling without loss. Results in Example 1, show that the wetted matrix is translucent enough for spectrometric determinations. Thus, nondestructive analysis is possible and quality assurance of the uniformity in product is practical.

Contact of the solution with the carrier, followed by drying, potentially can result in an irreversible dissociation of the drug:cyclodextrin inclusion complex and render the composition useless. Such dissociation may be caused by thermal changes or surface adsorption. The evaporation of water from such wetted absorbing materials, if performed at elevated temperature, will dissociate the inclusion complexes of drug with cyclodextrins and potentially separate the complex so it cannot form again. However, in Examples 1 and 2, it is shown that for one of the representative drugs investigated, irrespective of the dissociation of complexes at elevated temperatures, the final product is not affected. Experimental results unequivocally showed that moistening of the paper releases all the water soluble drug:cyclodextrin inclusion complex that was applied. On the other hand, dissociation of drug:cyclodextrin inclusion complex due to drug adsorption to the matrix was observed for amphotericin B: gamma cyclodextrin complex (Example 2). Only part of the amount of the drug deposited could be recovered by water; the rest had to be recovered by organic solvent. Nevertheless, even this complication does not make this particular combination impractical. The drug remaining in the complexed form was eluted easily and in constant amounts. Consequently, only total amounts of drug:cyclodextrin inclusion complex will have to be adjusted to achieve desirable doses.

For the dosage form to be practical, it must be stable. The absorbent paper carrying the drug:cyclodextrin inclusion complex was stored at room temperature and humidity for a prolonged period of time without obvious deterioration. Optionally, this product can be further stabilized by covering it with a protective layer of water soluble material (e.g., pharmaceutically acceptable gum or gelatine solutions). The products may also be supplied in small, sealed compartments.

The release of the drug:cyclodextrin inclusion complex from the carrier, for a dosage form to be practical, must be reproducible both in terms of time and amount eluted. In vitro evaluation of release in Example 2 showed that releases were reproducible in terms of time and occurred within a few minutes. Results also show that the amount of drug released rapidly is constant even when the phenomenon is complicated by adsorption. It should be noted that release within a few minutes is highly desirable for sublingual uses. For drugs for which slow release is desired, the release can be slowed by surface modification of the dosage form such as by covering the disk or tablet with compositions that swell and form a diffusion barrier, which slows the release.

The release of drug when evaluated in vivo must occur with all the positive attributes established in vitro (see Example 3). The sublingual release described in Example 3 leads to the presence of a solution of progesterone:hydroxypropyl-beta-cyclodextrin inclusion complex in the mouth for several minutes and that, according to the data in U.S. Pat. No. 4,596,795, leads to efficient transfer of the drug into blood circulation.

In some applications, it may be of advantage to use an absorbent matrix that disintegrates during administration. For such purposes, the approach described in Example 4 can be used. There the solution of drug in solution of cyclodextrin was absorbed into a tablet made from cellulose using hydroxypropyl beta-cyclodextrin as a binder. Alternatively, the solutions of drug:cyclodextrin inclusion complexes were absorbed into pharmaceutically acceptable powder to from a paste that can be processed by molding or extrusion. Both water soluble and water insoluble materials were used as powders.

The solid dosage forms of the present invention obviously provide advantages both in terms of production and clinical use. From the production point of view, the invented process eliminates the need for separate development of formulation methods for solid dosages of different drugs, as required when using previously existing technology. That is, powders of different drugs handle differently, but their solutions in cyclodextrin derivatives pour the same. The same processes and machinery could be used for many different drugs. Cleanup times of machinery between productions of different drugs can be expected to be much shorter—aqueous solutions are easier to wash off than are various powders.

From a clinical point of view, the present dosage forms provide means for evaluation of site and completeness of administration. When absorption must occur from the oral cavity, patients can be instructed not to swallow the eluted paper disk; thus, it can be checked for the completeness of elution from the matrix by disappearance from disk of a coloring agent which elutes from the disk in a manner similar to that of the drug:cyclodextrin inclusion complex. (Commercially available food coloring agents were found to elute from paper disks placed under tongue with rates from under one minute to over four minutes, a satisfactory range for the above purpose.)

Matrices of the invention may, as alternative to application within the oral cavity, be placed against any mucosal surface for absorption through the mucosa. Such forms may, for example, be administered vaginally, rectally, into the urethra or against the mucosa of the eye. Depending on the mucosa to which the dosage forms are to be applied, the shape of the matrices may be adapted into appropriate shapes. For example, tampons or thin cylinders may be appropriate for application to the vaginal, rectal or urethral mucosa.

EXAMPLE 1

Preparation of Disk-Like Dosage Forms

These forms were cut either from crepped filtration paper, product of Schleicher & Schuell, Germany, type 520 B or from polypropylene filtration cloth. In these preparations, either water or water:ethanol (1:2 by volume) were used as solvents. Cyclodextrins used were hydroxypropyl beta-cyclodextrin (HPBCD, product of Wacker Chemie GmbH, average 6.3 substituents per molecule), sulfopropyl-beta-cyclodextrin (product of Cyclolab Co., average 7 substituents per molecule) and gamma-cyclodextrin (product of American Maize Co.). Fifty percent solutions of HPBCD easily can be made in both these solvents and all these solutions have acceptable viscosity for the transfer by pipettes. Paper was easily wetted by both aqueous and aqueous ethanol solutions. Polypropylene repulsed the aqueous solutions, but was wetted by the aqueous ethanol.

To provide dosage forms from which absorption from mouth is critical, it was found that thin circular disks of less than 2 cm in diameter can be effectively used. A disk of 2 cm diameter of the above paper absorbs about 0.1 ml of a solution; that is, its carrying capacity is 3.6 mg per square cm or 0.2 mg per mg. A polypropylene disk of 2 cm diameter absorbs about 400 microliters. Disks wetted by 50% solutions of HPBCD were semitransparent and, after drying, had a glassy white appearance. No material was lost upon handling and disks did not get sticky upon storage in open air.

To prepare the dosage form, cyclodextrin was dissolved in water (50% solutions for HPBCD, 20% for gamma-cyclodextrin and sulfopropyl beta-cyclodextrin), or aqueous ethanol for HPBCD (50% solution). This solution was saturated with drug by intensive stirring for two hours. The suspension was then filtered and then spotted on paper or filtration cloth and air dried. The appearance and properties of these disks was the same as of disks carrying cyclodextrins only.

EXAMPLE 2

Release of Drugs From Disk Dosage Forms In Vitro

Paper disks of 2 cm diameter and carrying drug:cyclodextrin inclusion complexes in the amounts specified in Table 1 below were continuously eluted by water and the amount of drug eluted was measured by spectrophotometry. For progesterone, a wavelength of 240 nm was used. Data had to be corrected since paper contains a minor component which elutes rapidly and absorbs at this wavelength. Prewashing of paper removes this complication. Amphotericin B content was analyzed using wavelength 410 nm and data previously published (M. Kajtar et al., Biopolymers, 28, 1585–1596, 1989). Release of drug occurred into the first milliliters of eluent and was complete for progesterone, but only partial for amphotericin B. To confirm these conclusions, the eluted disks were dried and eluted by methanol (50 ml) overnight. No additional release was observed for progesterone, but further drug was release from amphotericin B disks was noted.

TABLE 1

| Drug | Cyclodextrin | Eluent Volume-% of Drug Released | | |
|---|---|---|---|---|
| Progesterone (4.1 mg) | HPBCD (50% solution) | 1.2 ml/90% | 2.9 ml/99% | 4.7 ml/99% |
| Progesterone (0.3 mg) | Sulfopropyl-BCD (20% solution) | 1.4 ml/95% | 3.2 ml/99% | 5.2 ml/100% |
| Amphotericin B (0.1 mg) | Gamma-CD (20% solution) | 1.1 ml/62% | 2.2 ml/63% | 4.4 ml/64% |

EXAMPLE 3

Release of Cyclodextrin and Drug From Disk Dosage Forms In Vivo

Paper disks of 2 cm diameter containing only HPBCD were kept under the tongue for 3 to 4 minutes and dried after retrieval. The disks were then extracted by water (50 ml) overnight and soluble carbohydrates in the extracts measured using anthrone reagent (Methods in Carbohydrate Chemistry, Volume 1, page 523, wavelength used 620 nm). HPBCD is reactive toward this reagent. The control paper disk with HPBCD, but not released under the tongue, registered 100 units (arbitrary scale); the empty paper disk registered 1.8 units; disks loaded with HPBCD and released for 3 to 4 minutes under the tongue, 1.6 units. Thus, the release of HPBCD into mouth is completed within a few minutes.

Paper disks carrying progesterone:HPBCD combination, prepared as in Example 2 were kept under the tongue and, after retrieval, dried and extracted by water (50 ml) overnight. Progesterone in the extracts was measured by spectrophotometry using methods and precautions as in Example 2. When progesterone extracted from the original disks (i.e., not released under tongue) is taken as 100%, disks which were released for 5 minutes under the tongue yielded 3.8% of the originally present progesterone, and disks released for 10 minutes, 3.2%. Several minutes under the tongue thus releases nearly all drug into the oral cavity.

EXAMPLE 4

Preparation of Tablet-like Dosage Form

Cellulose powder product of Macherey, Nagel & Co., Germany, type MN 300, average particle size 10 microns was used in generation of these forms; furthermore, commercial cornstarch, dextrose and lactose were used. Cyclodextrin solutions saturated with drug were made as in Example 1 and gradually added to these powders while homogenizing with a spatula until a toothpaste like consistency was obtained. This paste was then processed by molding and drying into tablet-like form suitable for oral administration. Tablets did not lose material upon handling. Alternatively, cellulose powder was wetted by dilute solution (1%) of HPBCD in water. Wetted powder was directly molded into tablets, which were dried. These preformed tablets retained some absorption capacity and were then saturated by small amounts of solutions of drugs made as described in Example 1.

I claim:

1. A process for preparation of solid dosage forms comprising the steps of:
    1) absorbing an aqueous solution containing at least one drug formulated as an inclusion complex with cyclodextrin into a matrix which will not disintigrate in water, and thereafter,
    2) evaporating water and any other volatiles from the matrix.

2. The process of claim 1 wherein at least one pharmaceutically acceptable coloring agent is also added to the solution during step 1.

3. The process of claim 2 wherein at least one pharmaceutically acceptable flavoring agent is present in the solution of step 1.

4. The process of claim 1 wherein, after step 2, the surface of the matrix is coated with a protective film.

5. The process of claim 1 wherein, after either step 1 or step 2, the matrix containing at least one active agent is divided into individual doses.

6. A process for preparation of a solid dosage form comprising the steps of:
    1) dissolving at least one biologically active agent which is capable of forming an inclusion complex with a cyclodextrin in water-containing solvent in which cyclodextrins are present at a concentration of 15% to 70%,
    2) moistening a pharmaceutically inert powder which will not disintegrate in water with the solution obtained in step 1,
    3) molding the product of step 2 into tablets, and
    4) drying tablets formed in step 3.

7. The process of claim 6 wherein, after step 4, the tablets are coated with a pharmaceutically acceptable coating material.

8. A matrix which will not disintegrate in water having absorbed thereon at least one drug which is in the form of an inclusion complex with a cyclodextrin.

9. The matrix of claim 8 which, additionally, contains imbedded therein a coloring agent which eluted from the solid matix in a manner similar to that of the drug:cyclodextrin inclusion complex.

10. The matrix of claim 8 which, additionally, contains imbedded therein a flavoring.

11. A solid matrix which will not disintegrate in water into which is imbedded at least one drug in the form of an inclusion complex with a cyclodextrin, at least one coloring agent which will elute at about the same rate as said cyclodextrin complex with said drug.

* * * * *